(12) United States Patent
Grass et al.

(10) Patent No.: US 10,485,498 B2
(45) Date of Patent: Nov. 26, 2019

(54) CONE BEAM COMPUTED TOMOGRAPHY PROJECTION VALUES PROVIDING SYSTEM AND METHOD

(71) Applicant: KONINKLIJKE PHILIPS N.V., Eindhoven (NL)

(72) Inventors: Michael Grass, Buchholz in der Nordheide (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/554,439

(22) PCT Filed: Jan. 19, 2017

(86) PCT No.: PCT/EP2017/051017
§ 371 (c)(1),
(2) Date: Aug. 30, 2017

(87) PCT Pub. No.: WO2017/129459
PCT Pub. Date: Aug. 3, 2017

(65) Prior Publication Data
US 2019/0105003 A1    Apr. 11, 2019

(30) Foreign Application Priority Data

Jan. 29, 2016 (EP) .................................... 16153341

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/4085* (2013.01);
(Continued)

(58) Field of Classification Search
CPC ..... A61B 6/032; A61B 6/4085; A61B 6/4233; A61B 6/4241; A61B 6/5205
See application file for complete search history.

(56) References Cited

U.S. PATENT DOCUMENTS

| 6,018,561 A | 1/2000 | Tam |
| 6,438,198 B1 | 8/2002 | Kohler |

(Continued)

FOREIGN PATENT DOCUMENTS

| EP | 15002548 | 2/2005 |
| EP | 1746540 | 1/2007 |

(Continued)

OTHER PUBLICATIONS

Roessl, et al., "K-edge imaging in x-ray computed tomography using multi-bin photon counting detectors", Phys. Med. Biol. 52 (2007) 4679-4696.

(Continued)

*Primary Examiner* — Mark R Gaworecki
(74) *Attorney, Agent, or Firm* — Larry Liberchuk

(57) ABSTRACT

The present invention relates to a projection values determination device (14) being adapted to determine a projection value for an x-ray of a cone beam (4) based on detection values generated by detection elements of a three-dimensional arrangement of detection elements, which have been traversed by the x-ray, and not based on a detection value generated by a detection element which has not been traversed by the x-ray. Hence, the projection values determination device does not determine a projection value for a respective x-ray based on a detection value generated by a detection element not traversed by the respective x-ray. In particular, also in the cone direction only detection values are considered for generating a projection value, which have been generated by detection elements which have really been traversed by the respective x-ray. This can lead to (Continued)

reduced cross talk and computed tomography images having an improved image quality.

14 Claims, 4 Drawing Sheets

(52) U.S. Cl.
CPC .......... *A61B 6/4233* (2013.01); *A61B 6/5205* (2013.01); *A61B 6/5258* (2013.01)

(56) References Cited

U.S. PATENT DOCUMENTS

| | | | |
|---|---|---|---|
| 7,190,758 | B2 | 3/2007 | Hagiwara |
| 7,639,775 | B2 | 12/2009 | Deman |
| 9,662,077 | B2 | 5/2017 | Moriyasu |
| 2003/0141906 | A1 | 7/2003 | Tumer |
| 2005/0082488 | A1 | 4/2005 | Mollov |
| 2007/0040125 | A1 | 2/2007 | Sato |
| 2010/0181491 | A1 | 7/2010 | Karim |
| 2013/0028379 | A1 | 1/2013 | Nelson |
| 2013/0248723 | A1 | 9/2013 | Virshup |
| 2013/0279785 | A1* | 10/2013 | Proksa ................. G06T 11/006 382/131 |
| 2015/0168570 | A1 | 6/2015 | Pelc |

FOREIGN PATENT DOCUMENTS

| | | |
|---|---|---|
| JP | 2007-175154 | 7/2007 |
| WO | 2010/032163 | 3/2010 |
| WO | 2012/080971 | 6/2012 |
| WO | 2014/180487 | 11/2014 |

OTHER PUBLICATIONS

Liu, et al., "Characterization of a silicon strip detector for photon-counting spectral CT using monoenergetic photons from 40 keV to 120 keV", Medical Imaging 2014.

* cited by examiner

CONE BEAM COMPUTED TOMOGRAPHY PROJECTION VALUES PROVIDING SYSTEM AND METHOD

CROSS REFERENCE TO RELATED APPLICATIONS

This application is the U.S. National Phase application under 35 U.S.C. § 371 of International Application No. PCT/EP2017/051017 filed Jan. 19, 2017, published as WO 2017/129459 on Aug. 3, 2017, which claims the benefit of European Patent Application Number 16153341.9 filed Jan. 29, 2016. These applications are hereby incorporated by reference herein.

FIELD OF THE INVENTION

The invention relates to a cone beam computed tomography projection values providing system and method. The invention relates further to a computer program for providing cone beam computed tomography projection values.

BACKGROUND OF THE INVENTION

In spectral cone beam computed tomography systems a radiation device for providing a cone beam, which is formed by x-rays, and a detector comprising a three-dimensional arrangement of detection elements for generating detection values are rotated around a rotational axis aligned with a subject, wherein a computed tomography image of the subject is reconstructed based on the generated detection values.

The detector comprises several two-dimensional orthogonal arrangements of detection elements, wherein each two-dimensional orthogonal arrangement of detection elements forms a respective plane of detection elements and wherein the planes of detection elements are parallel to the rotational axis and are aligned with the x-rays in the fan direction of the x-rays.

Detection values, which have been generated at different depths within the detector, correspond to different energies such that the detection values are spectral detection values. The quality of the spectral detection values can be reduced due to cross talk in the cone direction, which can lead to artifacts in the computed tomography image and hence to a reduced image quality.

SUMMARY OF THE INVENTION

It is an object of the present invention to provide a cone beam computed tomography projection values providing system which allows for a provision of cone beam computed tomography projection values, which can be used for reconstructing a computed tomography image having an improved image quality. It is a further object of the present invention to provide a corresponding cone beam computed tomography projection values providing system and a computer program for providing cone beam computed tomography projection values.

In a first aspect of the present invention a cone beam computed tomography projection values providing system for providing cone beam computed tomography projection values of a subject is presented, wherein the system comprises:

a detection values providing device for providing detection values, which have been generated by using a radiation device and a detector while a rotation device has rotated at least the radiation device and the subject relative to each other around a rotational axis, wherein the radiation device is adapted to provide a cone beam formed by x-rays and the detector comprises a three-dimensional arrangement of detection elements, wherein the detection elements are arranged for being traversed by the x-rays and are adapted to generate detection values depending on the x-rays having traversed the detection elements, a projection values determination device for determining projection values, wherein the projection values determination device is adapted to determine a projection value for an x-ray based on a detection value generated by a detection element traversed by the x-ray and not based on a detection value generated by a detection element not traversed by the x-ray.

In known cone beam computed tomography systems, when processing the detection values it is assumed that detection values generated by detection elements being arranged on top of each other in a depth direction of the detector belong to the same x-ray, although this assumption is not correct in the cone direction. This can lead to cross talk and corresponding artifacts in the computed tomography image. Since according to the present invention the projection values determination device is adapted to determine a projection value for an x-ray based on detection values generated by detection elements traversed by the x-ray and not based on a detection value generated by a detection element not traversed by the x-ray, for determining a projection value for an x-ray, detection values generated by detection elements arranged on top of each other in a depth direction are considered only, if these detection elements have really been traversed by the x-ray. In particular, also in the cone direction only detection values are considered for generating a projection value for a respective x-ray, which have been generated by detection elements which have really been traversed by the x-ray. This leads to reduced cross talk and computed tomography images having an improved image quality.

The detection values providing device can be a storing unit, in which the detection values are stored already, and from which the detection values can be retrieved for providing the same. The detection values providing device can also be a receiving unit for receiving the detection values from, for instance, a detection values acquisition unit and for providing the received detection values. The detection values providing device can also be the detection values acquisition unit itself.

The detector is preferentially a direct conversion semiconductor detector. In particular, the detector is an edge-on silicon strip detector like the edge-on silicon strip detector disclosed in the article "A Silicon-Strip Detector for Photon-Counting Spectral CT: Energy Resolution From 40 keV to 120 keV" by X. Liu et al., IEEE Transactions on Nuclear Science, volume 61, number 3, page 1099 to 1105 (2014), which is herewith incorporated by reference.

The projection values determination device is preferentially adapted to determine a projection value for a respective x-ray only based on one or several detection values generated by one or several detection elements traversed by the x-ray and to not determine any projection value based on one or several detection values generated by a detection element not traversed by the x-ray. Hence, preferentially all projection values are determined based on one or several detection values generated by one or several detection elements traversed by the x-ray and not based on one or several detection values generated by a detection element not traversed by the x-ray.

Preferentially, the system further comprises a reconstruction device for reconstructing a computed tomography image based on the determined projection values.

A cone beam has a fan direction and a cone direction, wherein to each x-ray of the cone beam a fan angle and a cone angle can be assigned. The cone angle of a respective x-ray may be defined as the angle between the respective x-ray and a central x-ray of the cone beam in the cone direction. The central x-ray is preferentially orthogonal to the rotational axis. The cone direction is preferentially parallel to the rotational axis. The fan angle of a respective x-ray may be defined as the angle between the respective x-ray and a central x-ray of the cone beam in the fan direction, wherein the fan direction is preferentially defined as a direction being orthogonal to the cone direction. A depth of a detection element within the detector is preferentially defined as a distance between an incidence surface of the detector and the respective detection element. The detector can comprise a three-dimensional arrangement of detection elements, wherein a three-dimensional position of a detection element may be defined by a position in the cone direction, a further position in the fan direction and a depth.

Preferentially, the detection elements are aligned with the x-rays in the fan direction and not aligned with the x-rays in the cone direction. In particular, the detector comprises several two-dimensional arrangements of detection elements, wherein each two-dimensional arrangement of detection elements forms a respective plane of detection elements, wherein the planes of detection elements are parallel to the rotational axis and are aligned with the x-rays in the fan direction and not aligned with the x-rays in the cone direction. Since the detection elements are aligned with the x-rays in the fan direction, cross talk in the fan direction can already be reduced by the geometrical construction of the detector. In a further embodiment the detection elements may also be aligned with the x-rays in the cone direction.

In an embodiment the planes of detection elements are arranged consecutively in the fan direction and alternately displaced such that the planes are alternately arranged at a first location and a second location, wherein the first location is closer to the radiation device than the second location. This allows the planes to be arranged very closely to each other in the fan direction and provides at the same time a lot of space for electrically connecting the detection elements as desired. This narrow arrangement of the planes in the fan direction allows for an accurate spatial sampling while generating the detection values, thereby further improving the quality of the projection values and hence of the finally reconstructed computed tomography image.

It is preferred that the radiation device is adapted to provide the cone beam such that it is alternately emitted from different emission locations which are arranged with an offset to each other along a direction being parallel to the rotational axis. This can increase the field of view of the computed tomography imaging process, wherein still the quality of the projection values and hence of the reconstructed computed tomography image is relatively high, because also in this case for determining a projection value for an x-ray only detection values are considered, which have really been traversed by this x-ray.

It is preferred that the detector and the projection values determination device are adapted such that a respective projection value is indicative of a number of photons of the x-rays. In particular, it is preferred that the detector and the projection values determination device are adapted such that the respective projection value is indicative of a number of photons of the respective x-ray, which are in a respective energy range, in order to provide spectral projection values. In a preferred embodiment the respective energy range depends on the depth of the respective detection element which has generated the respective detection value on which the determination of the respective projection value is based. For determining a projection value for an x-ray and for a certain energy range one or more detection values can be used, which have been generated by detection elements which are arranged at a depth, which corresponds to the energy range, and which have been traversed by the x-ray. If several detection values are used for determining a projection value, these detection values may be combined by, for instance, interpolation. The interpolation can include a weighting of the detection values, wherein the respective weight may depend on the distance of the center of the respective detection element to the center of the respective x-ray or on another measure like the degree of overlap of the respective x-ray and the respective detection element. In an embodiment a nearest-neighbor interpolation is used.

In an embodiment the respective energy range depends on the length of the respective x-ray from the incidence surface of the detector to the respective detection element which has generated the respective detection value on which the determination of the respective projection value is based. Thus, not just the depth of the respective detection element may be considered, but the real transmission length of a photon before being detected by a detection element may be considered when determining the energy range for the respective projection value. This can lead to an improved determination of the energy range for the respective photon and hence for the respective projection value. The respective energy range may depend on the cone angle of the respective x-ray. Since the transmission length of the respective photon through the detector before being detected by a detection element depends on the cone angle of the respective x-ray, the transmission length can relatively simply be considered by using the cone angle.

In a further aspect of the present invention a cone beam computed tomography projection values providing method for providing cone beam computed tomography projection values of a subject is presented, wherein the method comprises:
providing detection values by a detection values providing device, wherein the provided detection values have been generated by using a radiation device and a detector while a rotation device has rotated at least the radiation device and the subject relative to each other around a rotational axis, wherein the radiation device is adapted to provide a cone beam formed by x-rays and the detector comprises a three-dimensional arrangement of detection elements, wherein the detection elements are arranged for being traversed by the x-rays and are adapted to generate detection values depending on the x-rays having traversed the detection elements,
determining projection values by a projection values determination device, wherein the projection values determination device determines a projection value for an x-ray based on a detection value generated by a detection element traversed by the x-ray and not based on a detection value generated by a detection element not traversed by the x-ray.

In another aspect of the present invention a computer program for providing cone beam computed tomography projection values of a subject is presented, wherein the computer program comprises program code means for causing a cone beam computed tomography projection values providing system as defined in claim 1 to carry out the cone beam computed tomography projection values providing method as defined in claim 13, when the computer program is run on the cone beam computed tomography projection values providing system.

It shall be understood that the cone beam computed tomography projection values providing system of claim 1, the cone beam computed tomography projection values providing method of claim 13 and the computer program of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
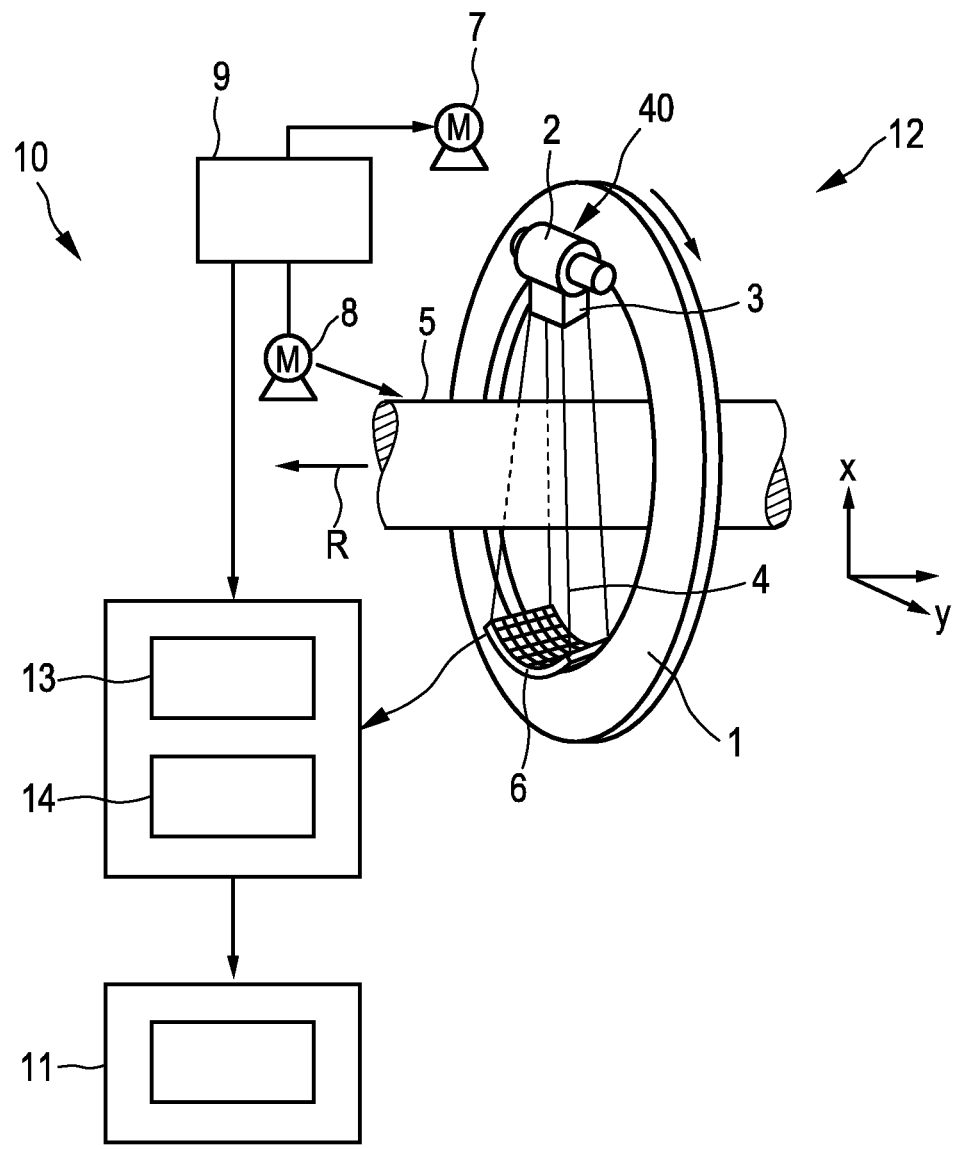
FIG. 1 shows schematically and exemplarily an embodiment of a cone beam computed tomography projection values providing system.

FIG. 1 shows schematically and exemplarily an embodiment of a cone beam computed tomography projection values providing system being, in this embodiment, a spectral cone beam computed tomography imaging system. The system 10 comprises a gantry 1 which is capable of rotation about a rotational axis R which extends parallel to the z direction. A radiation device 40, which comprises a radiation source 2 being, in this embodiment, an x-ray tube and a collimator 3, is mounted on the gantry 1. The collimator 3 forms a cone beam 4 from the radiation generated by the x-ray tube 2. The cone beam 4 traverses a subject within an examination zone 5 being, in this embodiment, cylindrical. After having traversed the examination zone 5 and hence the subject, the cone beam 4 is incident on a detector 6 which comprises a two-dimensional incidence surface, wherein the detector 6 is mounted on the gantry 1. The detector 6 is preferentially a direct conversion semiconductor detector, especially an edge-on silicon strip detector.

The system 10 comprises two motors 7, 8. The gantry 1 is driven at a preferably constant but adjustable angular of speed by the motor 7. The motor 8 is provided for displacing the subject arranged on a support means like a patient table in the examination zone 5 parallel to the direction of the rotational axis R or the z axis. These motors 7, 8 are controlled by a control unit 9, for instance, such that the radiation device 40 and the subject within the examination zone 5 move relative to each other along a helical trajectory. However, it is also possible that the radiation device 40 and the subject are moved relative to each other along another trajectory like a circular trajectory. The motor 7 and the gantry 1 are used for rotating the radiation device 40 and the detector 6 around the subject and may therefore be regarded as being components of a rotation device.

The detector 6 comprises a three-dimensional arrangement of detection elements, wherein the detection elements are arranged for being traversed by the x-rays of the cone beam 4 and are adapted to generate detection values depending on the x-rays having traversed the detection elements during the relative movement of the radiation device 40 and the subject.

Figure 2:
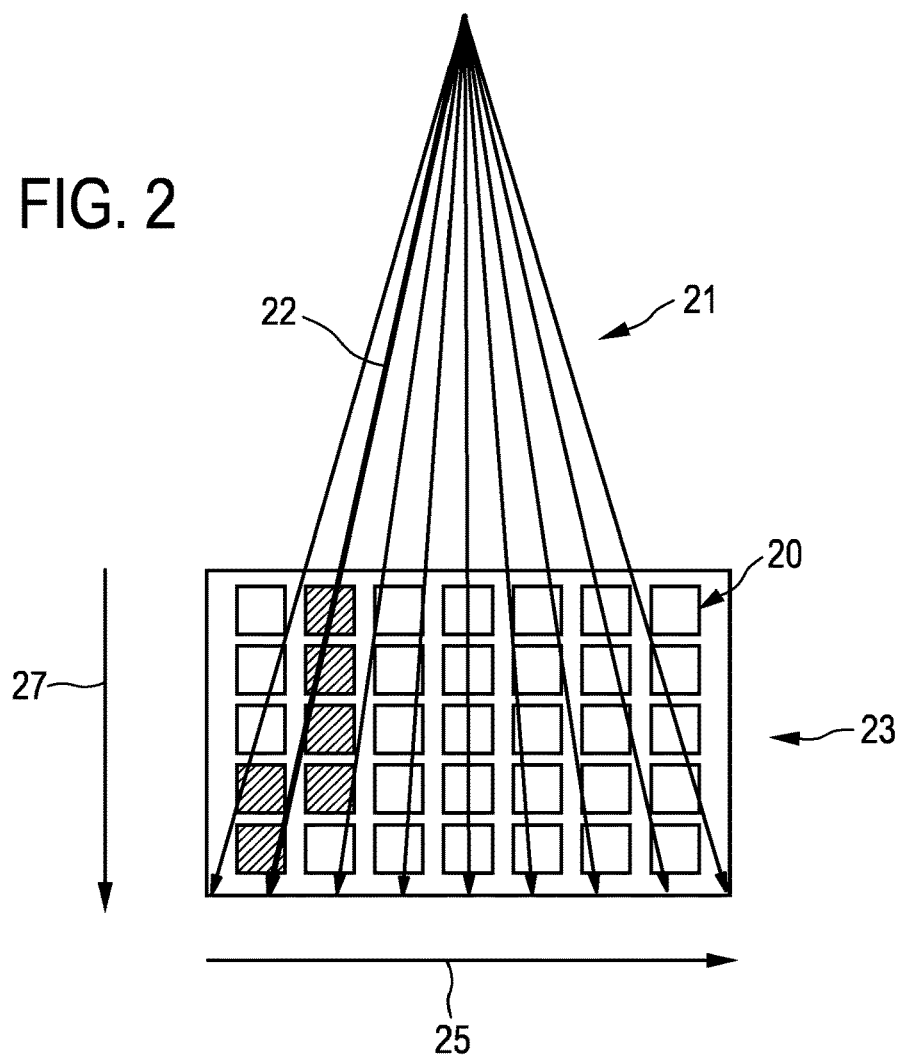
FIG. 2 shows schematically and exemplarily a two-dimensional arrangement of detection elements of a detector and x-rays of a cone beam.
Figure 3:
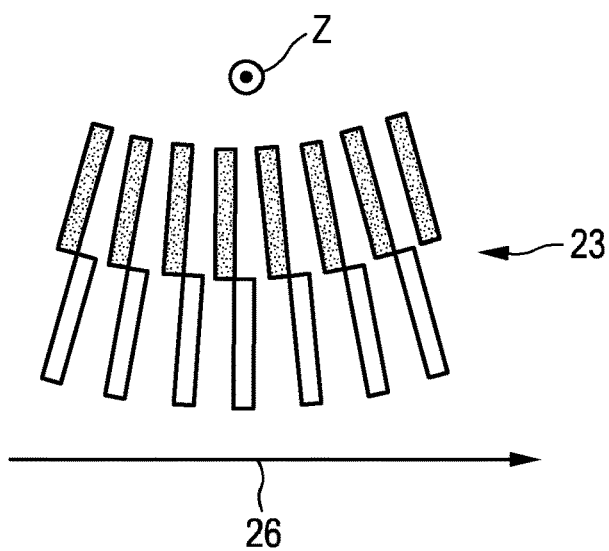
FIG. 3 illustrates schematically and exemplarily a detector geometry in the fan direction seen along a rotational axis.
Figure 4:
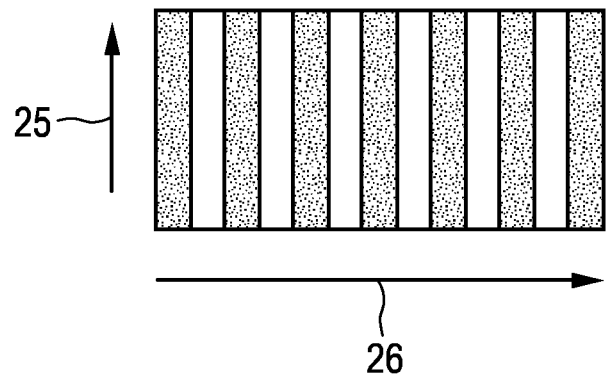
FIG. 4 illustrates schematically and exemplarily the same detector geometry as seen from a radiation device.

The detector 6 comprises several two-dimensional arrangements of detection elements 20 as schematically and exemplarily illustrated in FIGS. 3 and 4, wherein the several two-dimensional arrangements form the three-dimensional arrangement and a single two-dimensional arrangement is shown in FIG. 2. Each two-dimensional arrangement 23 of detection elements 20 forms a respective plane 23 of detection elements 20, which may also be regarded as being a respective slab 23 of detection elements 20, wherein the planes 23 of detection elements 20 are parallel to the rotational axis R and are aligned with the x-rays 21 in the fan direction 26 and not aligned with the x-rays 21 in the cone direction 25. The planes 23 of the detection elements 20 are arranged consecutively in the fan direction 26 and alternately displaced such that the planes 23 are alternately arranged at a first location and at a second location, wherein the first location is closer to the radiation device 40 than the second location, as schematically and exemplarily illustrated especially in FIG. 3. FIG. 3 illustrates a view on the planes 23 in the direction of the rotational axis R or the z axis and FIG. 4 illustrates a view on the planes 23 as seen from the radiation device 40. As illustrated in FIG. 2, within the respective plane 23 the detection elements 20 form a rectangular grid, wherein the detection elements are arranged in the cone direction 25 and at different depths. The direction of increasing depth is indicated by the arrow 27.

Since the radiation device 40 and the detector 6 generate the detection values while they are rotated around the subject, the radiation device 40 and the detector 6 can be regarded as being components of a detection values providing device being, in this embodiment, a detection values acquisition unit 12.

The detection values are provided to a projection values determination device 13 for determining projection values. The projection values determination device 13 is adapted to determine a projection value for a respective x-ray 22 based on a detection value generated by a detection element 20 traversed by the x-ray 22 and not based on a detection value generated by a detection element 20 not traversed by the x-ray 22. Preferentially, the projection values determination device 13 is adapted to determine for each respective x-ray 22 several projection values, which correspond to different energy ranges, based on the detection values generated by the detection elements 20 traversed by the respective x-ray 22. The projection value determined for a respective x-ray 22 and for a respective energy range is preferentially indicative of the number of photons of the respective x-ray 22, which are within the respective energy range. The detection elements 20 are arranged at different depths, i.e., for instance, at five different depths as schematically and exemplarily illustrated in FIG. 2. To each depth an energy range can be assigned such that for each x-ray 22 several projection values can be determined, which correspond to the different depths and hence to the different energy ranges. If the x-ray 22 traverses several detection elements at a same depth, the corresponding detection values can be combined for generating a projection value for this depth by, for instance, interpolation.

The x-rays forming the cone beam 4 can be defined by defining a number of x-rays in the cone direction 25 and by dividing the cone beam 4 accordingly such that they have the same divergent width. In the example schematically shown in FIG. 2 the cone beam 4 is divided into nine x-rays having a same divergent width, wherein in FIG. 2 the arrows 21, 22 denote the respective central lines of the respective x-rays having the divergent width and the detection elements 20 traversed by the x-ray 22 are highlighted. The x-ray 22 traverses at the three smallest depth positions and at the largest depth position a single detection element 20 only, but, since also the width of the x-ray 22 is considered, at the second largest depth position two detection elements 20 are traversed by the x-ray 22. Thus, in this example the detection values, which have been generated by these traversed detection elements in the second largest depth position, are combined for determining a projection value for the corresponding energy range and the x-ray 22.

In an embodiment the projection values determination device 13 is adapted to assign an energy range to a detection element 20 depending on the length of the respective x-ray 22 from the incidence surface of the detector 6 to the detection element 20. For instance, in FIG. 2 for determining the energy range for the detection element in the left lower corner within the two-dimensional arrangements of detection elements and for the x-ray 22 the length of the x-ray 22 within the detector 6 from the incidence surface 22 to the detection element 20 is determined and the energy range is determined based on this length, wherein with increasing length the energy range covers larger energies. In an embodiment the respective length is considered by defining the respective energy range based on the cone angle of the respective ray 22, wherein it is assumed that the acquisition geometry, especially the position of the radiation device 40 relative to the detection elements 20 is known.

The system 10 further comprises a reconstruction device 14 for reconstructing a computed tomography image of the subject based on the determined spectral projection values, wherein the reconstruction device 14 and also the projection values determination device 13 may be controlled by the control unit 9 or by another control unit. In this embodiment the reconstruction device 14 is adapted to use a filtered back projection algorithm for reconstructing the computed tomography image. The reconstruction device 14 can be adapted to use a material decomposition technique, in order to reconstruct different computed tomography images, which correspond to different materials within the person, based on the spectral projection values. For instance, if a contrast agent has been injected into the subject, a first image can be reconstructed only showing the contrast agent within the subject and a second image can be reconstructed showing the subject without the contrast agent. The reconstruction device 14 can also be adapted to reconstruct different computed tomography images, which correspond to different physical effects like the Compton Effect and the photoelectric effect, based on the spectral projection values. The reconstruction device 14 can of course also be adapted to use other spectral reconstruction techniques. Known reconstruction techniques, which might be used by the reconstruction device 14, are disclosed, for instance, in the article "K-edge imaging in x-ray computed tomography using multi-bin photon counting detectors" by E. Roessl and R. Proksa, Physics in Medicine and Biology, volume 52, pages 4679 to 4696 (2007). The reconstructed images can be shown on a display 11.

Figure 5:
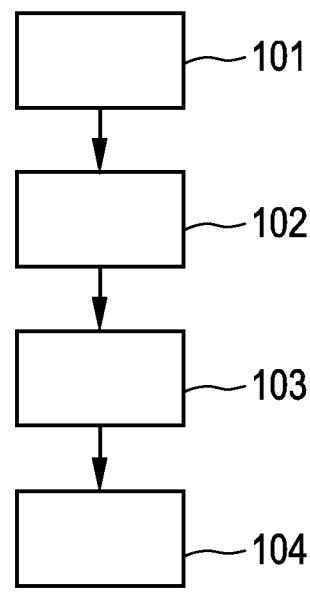
FIG. 5 shows a flowchart exemplarily illustrating an embodiment of a cone beam computed tomography projection values providing method.

In the following an embodiment of a cone beam computed tomography projection values providing method will exemplarily be described with reference to a flowchart shown in FIG. 5.

In this embodiment the cone beam computed tomography projection values providing method is a spectral cone beam computed tomography imaging method for generating a computed tomography image. In step 101 detection values are provided by the detection values acquisition unit 12. In particular, the radiation device 40 provides a cone beam 4 formed by x-rays 21 and the detection elements 20 of the detector 6 generate detection values depending on the x-rays 21 having traversed the detection elements 20.

In step 102 the projection values determination device 13 determines projection values based on the provided detection values, wherein a projection value is determined for a respective x-ray 22 based on a detection value generated by a detection element 20 traversed by the x-ray 22 and not based on a detection value generated by a detection element not traversed by the x-ray 22. In this embodiment the projection values determination device 13 determines for each x-ray and for different energy ranges projection values which are indicative of the number of photons of the respective x-ray, which are within the respective energy range. In step 103 the reconstruction device 14 reconstructs one or several computed tomography images based on the spectral projection values determined in step 102. In step 104 the one or several reconstructed computed tomography images are shown on the display 11.

Figure 6:
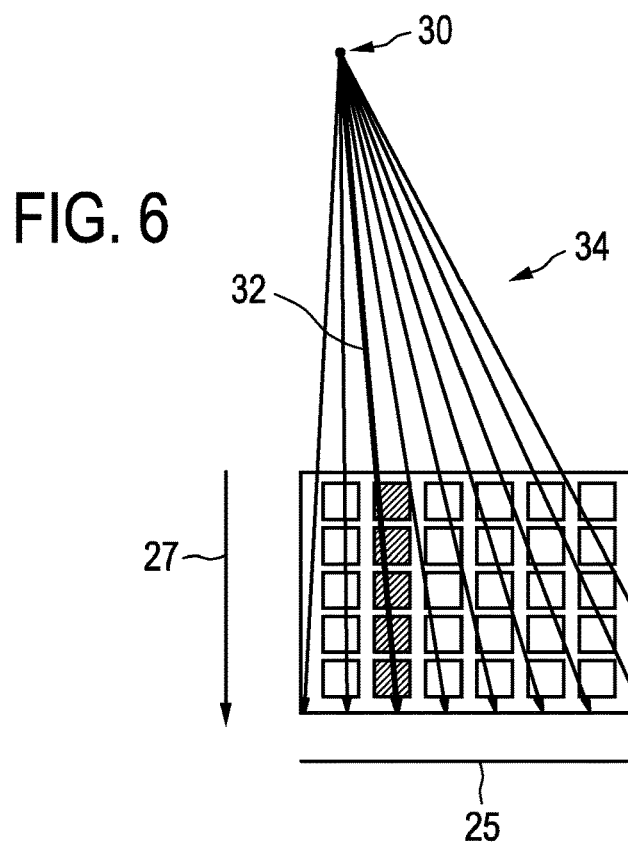
FIG. 6 shows schematically and exemplarily a two-dimensional arrangement of detection elements of a detector and x-rays emitted from a first emission location.
Figure 7:
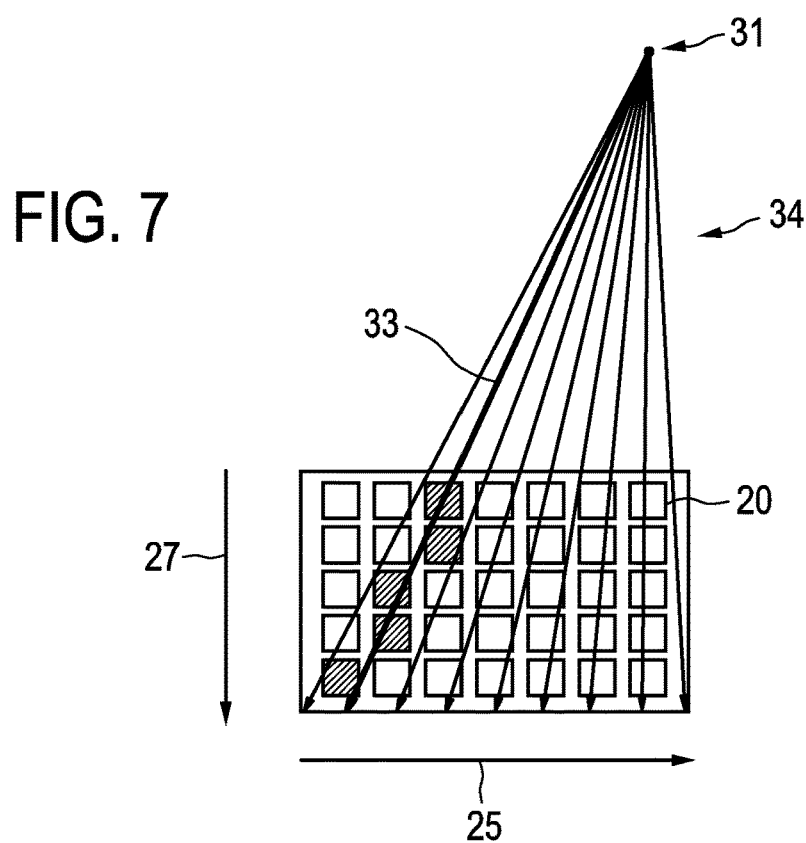
FIG. 7 shows schematically and exemplarily the two-dimensional arrangement of detection elements of the detector and x-rays emitted from a second emission location.

In an embodiment the radiation device 40 is adapted to provide the cone beam 4 such that it is alternately emitted from different emission locations which are arranged with an offset to each other along a direction being parallel to the rotational axis R. This is schematically and exemplarily illustrated in FIGS. 6 and 7, wherein in FIG. 6 the cone beam 4 comprising the x-rays 34 is emitted from a first emission location 30 and wherein in FIG. 7 the cone beam 4 with the x-rays 34 is emitted from a second location 31, wherein the first and second locations have an offset to each other in the z direction which corresponds to the cone direction 25. In FIGS. 6 and 7 the detection elements 20, which are traversed by the x-ray 32 and which therefore generate detection values, which are used for determining projection values for the x-ray 32, are highlighted. As can be seen in FIG. 6, because of the relatively small cone angle of the x-ray 32 only detection elements 20 on top of each other are considered. In FIG. 7 the x-ray 33 has a relatively large cone angle such that detection values, which have been generated by detection elements 20 of different columns, are considered for determining the projection values for the x-ray 33.

In known spectral cone beam computed tomography systems the above mentioned cross talk effect becomes more pronounced, if the cone angle becomes larger and/or if a stereo x-ray-tube, i.e. a radiation source alternately emitting the cone beam from different emission locations which are arranged with an offset to each other along a direction being parallel to the rotational axis, is used. In contrast to known readout patterns for reading out a detector with a three-dimensional arrangement of detection elements, in which it is assumed that detection elements being arranged on top of each other in the depth direction of the detector have been traversed by the same x-ray, the projection values determination device uses a modified readout pattern which is adapted to the actual x-ray geometry.

If the x-ray source does not change the emission location, at which the cone beam is emitted, relative to the radiation source, the x-ray geometry relative to the detector remains constant from view to view, i.e. from radiation source position to radiation source position while rotating the radiation device around the subject. The readout pattern used by the projection values determination device for determining the projection values based on the detection values can therefore also be constant. However, if the radiation source is a stereo x-ray tube, the x-ray geometry changes relative to the detector, when the emission location is changed relative to the radiation source, as illustrated in FIGS. 6 and 7. The readout pattern used by the projection values determination device for determining the projection values is therefore changed accordingly, in order to consider the detection values, which are used for determining the projection values for the x-rays, in accordance with the current x-ray geometry. This ensures that a projection value for an x-ray is determined based on one or several detection values, which have been generated by one or several detection elements which have really been traversed by the x-ray, and not based on a detection value generated by a detection element which has not been traversed by the x-ray. The readout pattern is therefore preferentially switched in accordance with the switching of the emission location of the cone beam provided by the stereo tube. This adaptation of the readout geometry to the x-ray geometry is preferentially performed only in the cone angle direction, i.e. in the cone direction, because preferentially the detection elements are already physically aligned to the x-ray geometry in the fan angle direction, i.e. in the fan direction.

FIG. 3 schematically and exemplarily illustrates the detector geometry in the fan direction 26 as seen along the rotational axis or the z axis. The same detector geometry as seen from the radiation device is illustrated in FIG. 4. FIG. 2 illustrates a single plane comprising a two-dimensional arrangement of detection elements, wherein this plane may be regarded as being a single edge-on silicon strip detector array. A pure Cartesian readout geometry does not match the geometry of the x-rays. In order to compensate for the cross talk which would occur when using a pure Cartesian readout, the projection values determination device is preferentially adapted to use a readout geometry which is in accordance with the x-ray geometry.

In the embodiment described above with reference to FIG. 2 five depth positions of the detection elements are present, wherein each depth position can correspond to a respective energy range. In another embodiment detection elements, which are arranged at different depth positions, can be read out together such that it is not distinguished between these different depth positions, i.e. neighboring depth positions can be combined and the detection elements arranged at these depth positions can be read out together, for instance, can be read out by a same application-specific integrated circuit (ASIC), in order to reduce the technical efforts for reading out the detection elements at the expense of a reduced depth and hence energy resolution. The physical width in the depth direction of a respective detection area comprising detection elements, which are read out together, can be different for different detection areas. In particular, this width can increase with increasing depth. Thus, the integration interval, i.e. the depth interval over which detection values are integrated, preferentially increases with increasing depth in the detector, in order to account for the energy dependence of the absorption depth.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of projection values or the reconstruction of a computed tomography image performed by one or several units or devices can be performed by any other number of units or devices. These operations and/or the control of the cone beam computed tomography projection values providing system in accordance with the cone beam computed tomography projection values providing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to a projection values determination device being adapted to determine a projection value for an x-ray of a cone beam based on detection values generated by detection elements of a three-dimensional arrangement of detection elements, which have been traversed by the x-ray, and not based on a detection value generated by a detection element which has not been traversed by the x-ray. Hence, the projection values determination device does not determine a projection value for a respective x-ray based on a detection value generated by a detection element not traversed by the respective x-ray. In particular, also in the cone direction only detection values are considered for generating a projection value, which have been generated by detection elements which have really been traversed by the respective x-ray. This can lead to reduced cross talk and computed tomography images having an improved image quality.

The invention claimed is:

1. A system for providing cone beam computed tomography projection values of a subject, the system comprising:
   a detection values providing device for providing detection values that are generated by using a radiation device and a detector while a rotation device rotates at least the radiation device and the subject relative to each other around a rotational axis, wherein the radiation device is configured to provide a cone beam formed by x-rays, wherein the detector comprises a three-dimensional arrangement of detection elements, and wherein the detection elements are arranged for being traversed by the x-rays and configured to generate the detection values depending on the x-rays having traversed the detection elements; and
   a projection values determination device configured to determine a projection value for an x-ray based on a detection value generated by a detection element traversed by the x-ray and not based on another detection value generated by another detection element not traversed by the x-ray.

2. The system as defined in claim 1, wherein the detection elements are aligned with the x-rays in a fan direction and not aligned with the x-rays in a cone direction.

3. The system as defined in claim 1, wherein the detector comprises several two-dimensional arrangements of the detection elements, wherein each two-dimensional arrangement of the detection elements forms a respective plane of the detection elements, wherein the planes of the detection elements are parallel to the rotational axis and aligned with the x-rays in a fan direction and not aligned with the x-rays in a cone direction.

4. The system as defined in claim 3, wherein the planes of the detection elements are arranged consecutively in the fan direction and alternately displaced such that the planes are alternately arranged at a first location and a second location, wherein the first location is closer to the radiation device than the second location.

5. The system as defined in claim 1, wherein the radiation device is configured to provide a cone beam alternately emitted from different emission locations which are arranged with an offset to each other along a direction parallel to the rotational axis.

6. The system as defined in claim 1, wherein the detector and the projection values determination device are configured such that a respective projection value is indicative of a number of photons of the x-rays.

7. The system as defined in claim 6, wherein the detector and the projection values determination device are configured such that the respective projection value is indicative of the number of photons of the respective x-ray, which are in a respective energy range, in order to provide spectral projection values.

8. The system as defined in claim 7, wherein the respective energy range depends on a depth of the respective detection element that generated the respective detection value on which a determination of the respective projection value is based.

9. The system as defined in claim 7, wherein the respective energy range depends on a length of the respective x-ray from an incidence surface of the detector to the respective detection element that generated the respective detection value on which a determination of the respective projection value is based.

10. The system as defined in claim 7, wherein the respective energy range depends on a cone angle of the respective x-ray.

11. The system as defined in claim 1, wherein the detector is a direct conversion semiconductor detector.

12. The system as defined in claim 1, further comprising a reconstruction device for reconstructing a computed tomography image based on the determined projection values.

13. A method for providing cone beam computed tomography projection values of a subject, the method comprising:
providing detection values by a detection values providing device, wherein the provided detection values are generated by using a radiation device and a detector while a rotation device rotates at least the radiation device and the subject relative to each other around a rotational axis, wherein the radiation device is configured to provide a cone beam formed by x-rays wherein the detector comprises a three-dimensional arrangement of detection elements, and wherein the detection elements are arranged for being traversed by the x-rays and configured to generate detection values depending on the x-rays having traversed the detection elements; and
determining projection values by a projection values determination device for an x-ray based on a detection value generated by a detection element traversed by the x-ray and not based on another detection value generated by another detection element not traversed by the x-ray.

14. A non-transitory computer-readable medium having one or more executable instructions stored thereon, which, when executed by at least one processor, cause the at least one processor to perform a method for providing cone beam computed tomography projection values of a subject, the method comprising:
providing detection values by a detection values providing device, wherein the provided detection values are generated by using a radiation device and a detector while a rotation device rotates at least the radiation device and the subject relative to each other around a rotational axis, wherein the radiation device is configured to provide a cone beam formed by x-rays, wherein the detector comprises a three-dimensional arrangement of detection elements, and wherein the detection elements are arranged for being traversed by the x-rays and configured to generate detection values depending on the x-rays having traversed the detection elements; and
determining projection values by a projection values determination device for an x-ray based on a detection value generated by a detection element traversed by the x-ray and not based on another detection value generated by another detection element not traversed by the x-ray.

* * * * *